N. B. McGRATH.
SQUARE.
APPLICATION FILED OCT. 19, 1910.
Reissued May 9, 1911.
13,236.
Fig 1.
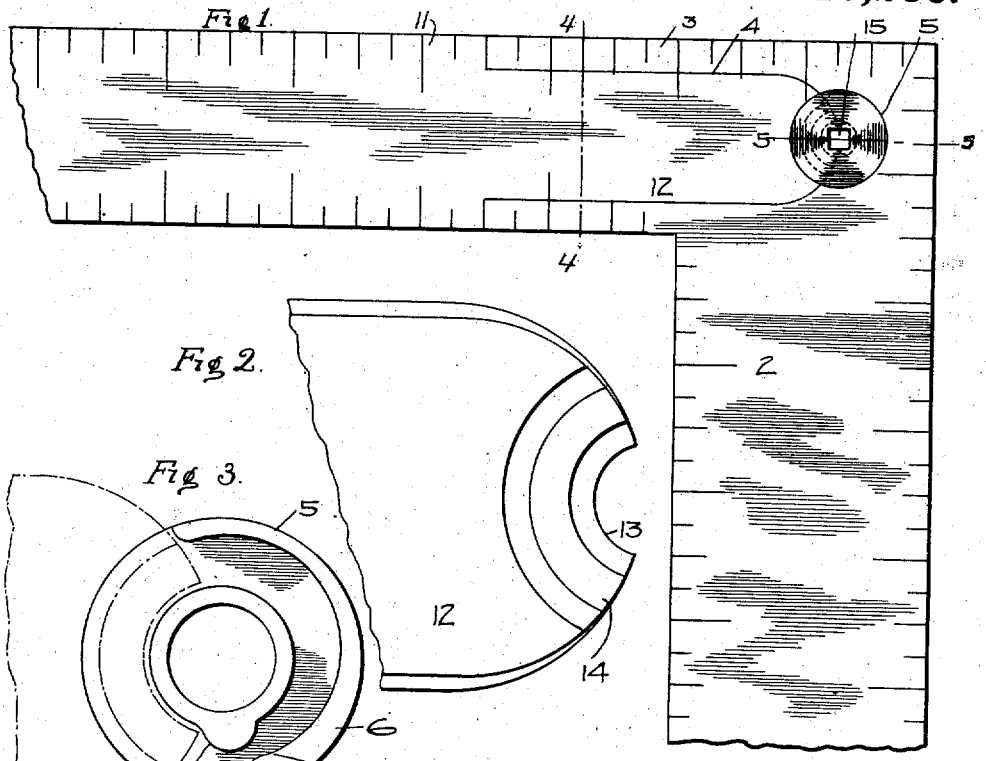
Fig 2.
Fig 3.
Fig 4.
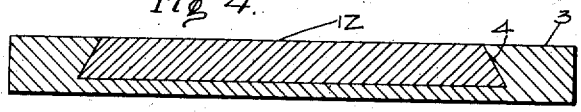
Fig 5
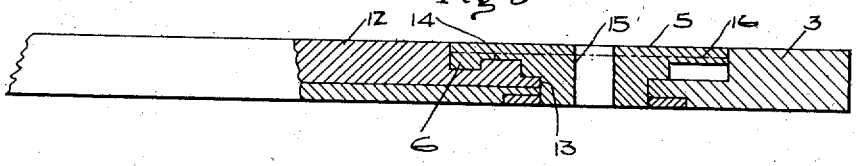
WITNESSES:
R. Burt M. Sess
Jno. T. Obulin
INVENTOR
Nicholas B. McGrath
BY
J. B. Fay
ATTORNEY
THE NORRIS PETERS CO., WASHINGTON, D. C.

UNITED STATES PATENT OFFICE.

NICHOLAS B. McGRATH, OF SOUTHINGTON, CONNECTICUT.

SQUARE.

13,236. Specification of Reissued Letters Patent. Reissued May 9, 1911.

Original No. 964,998, dated July 19, 1910, Serial No. 557,356. Application for reissue filed October 19, 1910. Serial No. 587,997.

*To all whom it may concern:*

Be it known that I, NICHOLAS B. McGRATH, a citizen of the United States, residing at Southington, in the county of Hartford and State of Connecticut, have invented a new and useful Improvement in Squares; and I do hereby declare the following, when taken in connection with the accompanying drawings and the numerals of reference marked thereon, to be a full, clear, and exact description of the same, and which said drawings constitute part of this specification, and represent, in—

Figure 1 a plan view of a square constructed in accordance with my invention. Fig. 2 an enlarged plan view of the inner end of the finger of the tongue. Fig. 3 an underside view of the locking block. Fig. 4 a sectional view on the line 4—4 of Fig. 1. Fig. 5 a sectional view on the line 5—5 of Fig. 1.

This invention relates to an improvement in squares, and particularly to squares of the so called take-down type; that is, a square in which the tongue is separable from the body.

The object of this invention is to provide simple and convenient means whereby the tongue may be firmly interlocked with the body; and the invention consists in the construction hereinafter described and particularly recited in the claims.

In carrying out my invention the body 2 is formed with a head 3 slightly projecting beyond the body, and extending across the face of the head and upper end of the body is an undercut recess or groove 4, and mounted at the inner end of the recess is a rotating locking-block 5 formed in its under face with an engaging element in the form of a spiral rib 6 having a stop-surface 9 and with a cam 10 for the purpose as will hereinafter appear. The tongue 11 at one end is formed with a finger 12 having beveled edges adapted to closely fit in the groove 4. This finger is arranged at its inner end and formed with a centrally arranged notch 13 to clear the locking-block 5 and the face of the finger is cut away to extend beneath the surface of the block, and in this cut-away portion is an engaging element formed by a segmental rib 14 so as to be complementary to the element on the locking block. The finger 12 is inserted into the groove 4, the block 5 being turned so that the rib 6 will not obstruct its movement. When in substantially the limit of its inward movement the block 5 is turned causing the rib 6 to engage with the segmental rib 14 and draw the tongue firmly into engagement with the body, the stop-surface 9 preventing the complete rotation of the block 5. The block 5, as I may state, is provided with a central angular opening 15, or it may be formed with a transverse slot 16 as shown in broken lines Fig. 5, for the introduction of a screw driver or other convenient tool by which the block may be turned. The tongue is therefore drawn into position and locked by the block. The fit of the finger 12 in the groove 4 must be a very close one, and consequently the tongue cannot be readily removed even when the block is turned, and to facilitate its removal the cam 10 will when the block is moved into its unlocking position, engage with one end of the rib 14 and force the finger 12 slightly outward so that the tongue may be more conveniently withdrawn.

I claim:—

1. In a square, the combination of a body formed with an undercut groove; a rotatable locking block mounted adjacent to said groove; and a tongue having its one end adapted to be entered into said groove, said locking block and tongue-end being formed with complementary ribs and grooves adapted to engage so that when the block is turned, the tongue will be locked to the body.

2. In a square, the combination of a body formed at one end with an undercut groove; a rotatable locking block mounted at the inner end of said groove and formed in one face with a rib; and a tongue having a finger adapted to be entered into said groove and formed with a rib with which the rib of the locking block may engage, whereby, when the block is turned, the tongue will be locked to the body.

3. In a square, the combination with a body formed at its upper end with an undercut groove, a rotatable locking block mounted at the inner end of said groove and formed in its inner face with a rib, combined with a tongue having a beveled finger adapted to be entered into said groove, notched at its inner end to clear said locking block, and formed with a segmental rib with which the rib of the locking block may engage, whereby when the block is turned the tongue will be locked to the body.

4. In a square, the combination with a body formed at its upper end with an undercut groove, a rotatable locking block mounted at the inner end of said groove and formed in its inner face with a segmental rib having a spiral surface, and with a cam, combined with a tongue having a beveled finger adapted to be entered into said groove, notched at its inner end to clear said locking block and formed with a segmental rib with which the rib of the locking block may engage and with the end of which the said cam may engage, whereby when the block is turned the tongue will be locked to the body or forced outward therefrom.

In testimony whereof, I have signed this specification in the presence of two subscribing witnesses.

NICHOLAS B. McGRATH.

Witnesses:

THOMAS F. WELCH,

GEO. F. SMITH.

Copies of this patent may be obtained for five cents each, by addressing the "Commissioner of Patents, Washington, D. C."